(12) United States Patent
Fujikawa et al.

(10) Patent No.: US 7,862,998 B2
(45) Date of Patent: Jan. 4, 2011

(54) ASSIST PROBE AND METHOD OF USING THE SAME

(75) Inventors: Toshihiko Fujikawa, Kawasaki (JP); Mitsugu Usui, Yokohama (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 35 days.

(21) Appl. No.: 11/885,226

(22) PCT Filed: Feb. 27, 2006

(86) PCT No.: PCT/JP2006/303629
§ 371 (c)(1),
(2), (4) Date: Aug. 28, 2007

(87) PCT Pub. No.: WO2006/093097

PCT Pub. Date: Sep. 8, 2006

(65) Prior Publication Data
US 2008/0160624 A1    Jul. 3, 2008

(30) Foreign Application Priority Data
Feb. 28, 2005 (JP) ............................. 2005-054521

(51) Int. Cl.
C12Q 1/68 (2006.01)
(52) U.S. Cl. ......................................................... 435/6
(58) Field of Classification Search .................. None
See application file for complete search history.

(56) References Cited

U.S. PATENT DOCUMENTS

| | | | |
|---|---|---|---|
| 5,175,270 A * | 12/1992 | Nilsen et al. | ............ 536/24.32 |
| 5,474,796 A * | 12/1995 | Brennan | .................... 427/2.13 |
| 6,261,846 B1 * | 7/2001 | Usui | .............................. 436/94 |
| 6,589,726 B1 | 7/2003 | Butler et al. | |
| 2003/0008294 A1 | 1/2003 | Usui et al. | |
| 2006/0035235 A1 | 2/2006 | Usui et al. | |

FOREIGN PATENT DOCUMENTS

| | | |
|---|---|---|
| AU | 2004212083 | 8/2004 |
| CA | 2 515 734 | 8/2004 |
| CA | 2 516 360 | 9/2004 |
| CN | 1745180 | 3/2006 |
| EP | 1 593 746 | 11/2005 |
| JP | 2000-201687 | 7/2000 |
| JP | 3267576 | 1/2002 |
| JP | 3310662 | 5/2002 |
| KR | 10-2005-0103904 | 11/2005 |
| WO | 01/75157 | 10/2001 |
| WO | 03/029441 | 4/2003 |
| WO | 2004/072302 | 8/2004 |
| WO | 2004/074480 | 9/2004 |

OTHER PUBLICATIONS

New England Biolabs 1998/99 Catalog (NEB Catalog).*
Canadian Office Action issued Jul. 30, 2009 in corresponding Canadian Application No. 2,599,537.
European Extended Search Report issued Jan. 5, 2010 in corresponding European Application No. 06 71 4766.
Database Geneseq [Online], "Steroid hormone receptor analogue ECDN mRNA RT-PCR primer", XP002560188, Nov. 6, 1996, retrieved from EBI accession No. GSN: AAT27619.
M. Collins et al., "A branched DNA signal amplification assay for quantification of nucleic acid targets below 100 molecules/ml", Nucleic Acids Research, 1997, vol. 25, No. 15, pp. 2979-2984.

* cited by examiner

*Primary Examiner*—Christopher M. Babic
(74) *Attorney, Agent, or Firm*—Wenderoth, Lind & Ponack, L.L.P.

(57) ABSTRACT

Provided are a method of detecting target genes capable of increasing sensitivity in a Palsar method and of simultaneously detecting multiple genes, an assist probe to be used in the above method, and a method of forming a signal probe polymer by using the assist probe. The method of detecting target genes includes: forming a signal probe polymer by using a first probe having a nucleic acid region X, a nucleic acid region Y and a nucleic acid region Z in the stated order from the 5' end, a second probe having a nucleic acid region X', a nucleic acid region Y' and a nucleic acid region Z' in the stated order from the 5' end, and an assist probe having a plurality of the same nucleic acid regions as in the first probe and a target region capable of hybridizing with a target gene. In this method, the assist probes are designed so as to have a structure including the nucleic acid regions X, Y and X, and the target region in the stated order from the 5' end or a structure including the target region, and the nucleic acid regions Z, Y and Z in the stated order from the 5' end.

8 Claims, 9 Drawing Sheets

(a)

(b)

ASSIST PROBE AND METHOD OF USING THE SAME

This application is a U.S. national stage of International Application No. PCT/JP2006/303629 filed Feb. 27, 2006.

TECHNICAL FIELD

The present invention relates to an assist probe to be used in a signal amplification method using a pair of oligonucleotides that form a self-assembly substance and a method of using the same. More specifically, the present invention relates to an assist probe capable of increasing sensitivity and of simultaneously detecting a plurality of genes in a case where the signal amplification method is used on a DNA tip including a support in a form of a microplate, glass slide, fine particle, electroconductive substrate (hereinafter, collectively referred to as a DNA tip), a method of detecting a target gene by using the assist probe, and a method of forming a signal probe polymer by using the assist probe.

BACKGROUND ART

As signal amplification methods without using any enzyme, there have been reported a signal amplification method using a pair of oligonucleotides (hereinafter, referred to as HCPs) represented by the following chemical formulae (1) and (2) to form a self-assembly substance (polymer) of the HCPs (hereinafter, referred to as a PALSAR method) and a method of detecting genes using the method (Patent Documents 1 and 2, etc.).

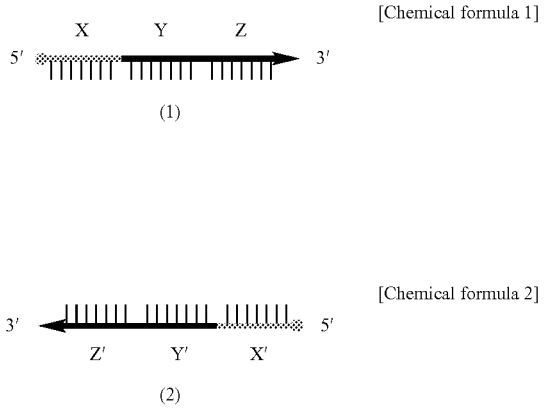

In the formulae (1) and (2), the region X and X', the region Y and Y', and the region Z and Z' are complementary nucleic acid regions capable of hybridizing with each other, and a self-assembly substance represented by the following chemical formula (3) is formed by binding plural pairs of HCPs. In the present specification, the signal probe polymer refers to the self-assembly substance formed from HCPs. Meanwhile, the assist probe refers to a probe, which has both a sequence complementary to that of a target gene to be detected and a sequence complementary to that of an HCP, and plays a role in linking the target gene to a signal probe polymer.

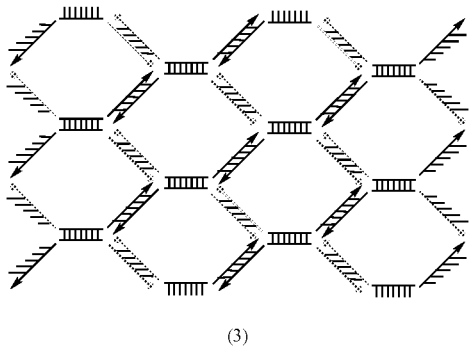

Meanwhile, Patent Document 3 discloses a method of detecting a target gene on a DNA tip by using the PALSAR method. Patent Documents 1 to 3 disclose methods of sensitively detecting a target gene by forming a complex of a target gene and a self-assembly substance to detect the self-assembly substance. A method of forming a signal probe polymer on a target gene includes a method of designing an HCP so as to have a sequence complementary to that of a target gene, and a method of using an assist probe. Of those, the method of forming an assist probe has an advantage of being capable of detecting a plurality of genes with a pair of HCPs by preparing a plurality of assist probes modified so as to have different sequences complementary to that of a target gene.

In each of Patent Documents 1 to 3, an assist probe having a sequence complementary to that of one region in an HCP is illustrated, but an assist probe capable of sensitively detecting a target gene have not been clarified.

[Patent Document 1] JP 3267576 B
[Patent Document 2] JP 3310662 B
[Patent Document 3] WO 2003-029441
[Patent Document 4] WO 2004-074480
[Patent Document 5] WO 2004-072302

DISCLOSURE OF THE INVENTION

Problems to be Solved by the Invention

In view of the present state of the related art, the inventors of the present invention have made extensive studies to increase detection sensitivity in the PALSAR method and to simultaneously detect many kinds of genes. As a result, they have found out a method of designing an assist probe suitable for the PALSAR method. It is an object of the present invention to provide a method of detecting a target gene, capable of increasing sensitivity in the PALSAR method and of simultaneously detecting many genes, an assist probe to be used in the method, and a method of forming a signal probe polymer using the assist probe.

Means for Solving the Problems

In order to solve the above-mentioned problems, the inventors of the present invention have made extensive studies on a design of an assist probe. As a result, they have found out a method of designing an assist probe most suitable for the PALSAR method, thus completing the present invention. That is, the present invention provides a method of detecting a target gene, including forming a signal probe polymer by using:

a pair of first and second probes (also referred to as HCPs) including:
a first probe (also referred to as HCP-1) having three nucleic acid regions, which includes a nucleic acid region X, a nucleic acid region Y, and a nucleic acid region Z in the stated order from the 5' end and has a structure represented by the following chemical formula (1);

[Chemical formula 4]

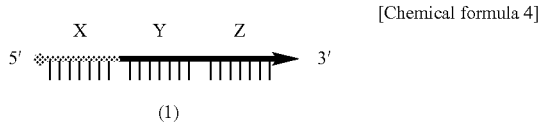

(1)

a second probe (also referred to as HCP-2) having three nucleic acid regions, which includes a nucleic acid region X', a nucleic acid region Y', and a nucleic acid region Z' in the stated order from the 5' end and has a structure represented by the following chemical formula (2)

[Chemical formula 5]

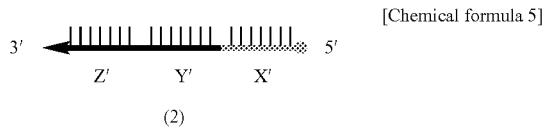

(2)

in the chemical formulae (1) and (2), the nucleic acid regions X and X', the nucleic acid regions Y and Y', and the nucleic acid regions Z and Z' are complementary regions capable of hybridizing with each other, respectively; and
an assist probe having a plurality of the same nucleic acid regions as in the first probe and a target region capable of hybridizing with a target gene,
in which the assist probe has a structure including the nucleic acid regions X, Y, and X, and the target region in the stated order from the 5' end, or a structure including the target region, and the nucleic acid regions Z, Y, and Z in the stated order from the 5' end.

As the assist probe, there may used an assist prove having a spacer region incapable of hybridizing with the target gene and the first and second probes between the target region and the nucleic acid region X or Z.

Further, as the assist probe, there may used an assist probe including a XYX region having the nucleic acid regions X, Y, and X, a YX region having the nucleic acid regions Y and X, and the target region in the stated order from the 5' end.

It is preferable that the assist probe further includes a spacer region incapable of hybridizing with the target gene and the first and second probes between the XYX region and the YX region or between the ZY region and the ZYZ region.

Meanwhile, as the assist probe, there may be used an assist probe that includes the target region, a ZY region having the nucleic acid regions Z and Y, and a ZYZ region having the nucleic acid regions Z, Y, and Z in the stated order from the 5' end.

Preferably, the assist probe further includes a spacer region incapable of hybridizing with a target gene and the first and second probes between the ZY region and the ZYZ region.

The method of detecting a target gene of the present invention may include a reaction step of performing a ligation reaction for the assist probes by using the target gene as a template, which enables detection of the target gene by the hybridization reaction.

Meanwhile, the method of detecting a target gene of the present invention may include a reaction step of reverse transcription by using the assist probes each having poly(dT) or a primer sequence in a target region on the 3' end side as primers and using a target RNA as a template, which enables detection of a target gene by the reverse transcription reaction.

In the method of detecting a target gene of the present invention, a plurality of assist probes, which are different from each other only in the target regions, are used, thereby being capable of simultaneously detecting a plurality of target genes.

A method of forming a signal probe polymer according to the present invention includes: using a pair of first and second probes including:
a first probe having three nucleic acid regions, which includes a nucleic acid region X, a nucleic acid region Y, and a nucleic acid region Z in the stated order from the 5' end, and has a structure represented by the following chemical formula (1);

[Chemical formula 6]

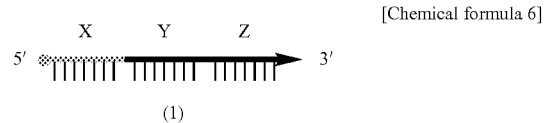

(1)

a second probe having three nucleic acid regions, which includes a nucleic acid region X', a nucleic acid region Y', and a nucleic acid region Z' in the stated order from the 5' end and has a structure represented by the following chemical formula (2)

[Chemical formula 7]

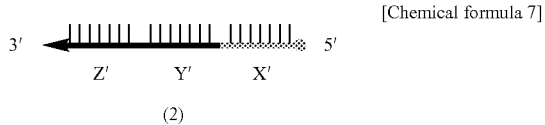

(2)

in the chemical formulae (1) and (2), the nucleic acid regions X and X', the nucleic acid regions Y and Y', and the nucleic acid regions Z and Z' are complementary regions capable of hybridizing with each other, respectively; and
an assist probe having a plurality of the same nucleic acid regions as in the first probe and a target region capable of hybridizing with a target gene; and
allowing plural pairs of the first and second probes, the assist probes, and the target gene to react with each other,
in which the assist probe has a structure including the nucleic acid regions X, Y, and X, and the target region in the stated order from the 5' end, or a structure including the target region, and the nucleic acid regions Z, Y, and Z in the stated order from the 5' end.

A first aspect of the assist probe of the present invention provides an assist probe to be used in the above-mentioned method according to the present invention, characterized in that the assist probe includes a XYX region having the nucleic acid regions X, Y, and X and the target region in the stated order from the 5' end.

As the assist probe described above, there may be used an assist probe that includes the target region with poly(dT) or a primer sequence.

As the assist probe described above, there may be also used an assist probe that further includes a YX region having the nucleic acid regions Y and X, and/or a spacer region incapable of hybridizing with a target gene and the first and second probes between the XYX region and the target region.

A second aspect of the assist probe of the present invention provides an assist probe to be used in the above-mentioned method according to the present invention, characterized in the assist probe has a structure including the target region and a ZYZ region having the nucleic acid regions Z, Y, and Z in the stated order from the 5' end.

As the assist probe described above, there may be used an assist probe having a phosphate group at the 5' end on the target region side.

As the assist probe described above, there may be also used an assist probe that further includes a YZ region having the nucleic acid regions Y and Z, and/or a spacer region incapable of hybridizing with a target gene and the first and second probes between the ZYZ region and the target region.

A signal probe polymer of the present invention is characterized by being formed by the above-mentioned method according to the present invention.

Effect of the Invention

According to the present invention, it is possible to significantly increase sensitivity in detection of a target gene using the PALSAR method. Meanwhile, by changing the target regions of the assist probes of the present invention, it is possible to simultaneously detect various kinds of genes.

Figure 1:
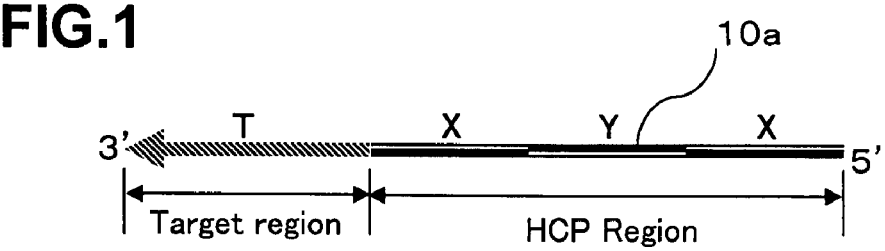
FIG. 1 is a schematic diagram illustrating a first example of an assist probe of the present invention.

DESCRIPTION OF REFERENCE NUMERALS 10a to 10h: assist probe of the present invention, 11a, 11b: assist probe, 12, 12a, 12b: target gene, 14: HCP-2, 16: HCP-1, 18: signal probe polymer, 20: capture probe, 22: support, 24: adjacent part between assistant probe 10g and capture probe 20, 26: probe

BEST MODE FOR CARRYING OUT THE INVENTION

Hereinafter, embodiments of the present invention will be described with reference to the accompanying drawings, which are for illustrative purposes only, and it will be appreciated that various modifications can be made without departing from the technical idea of the invention.

Figure 2:
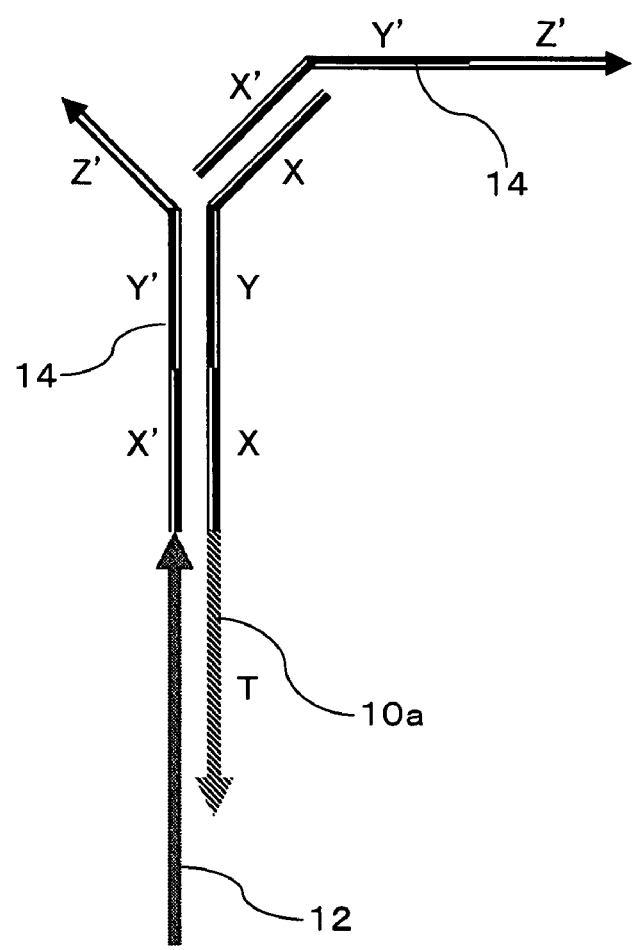
FIG. 2 is a schematic diagram illustrating a state where HCP-2 and a target gene bind to the assist probe of FIG. 1.
Figure 3:
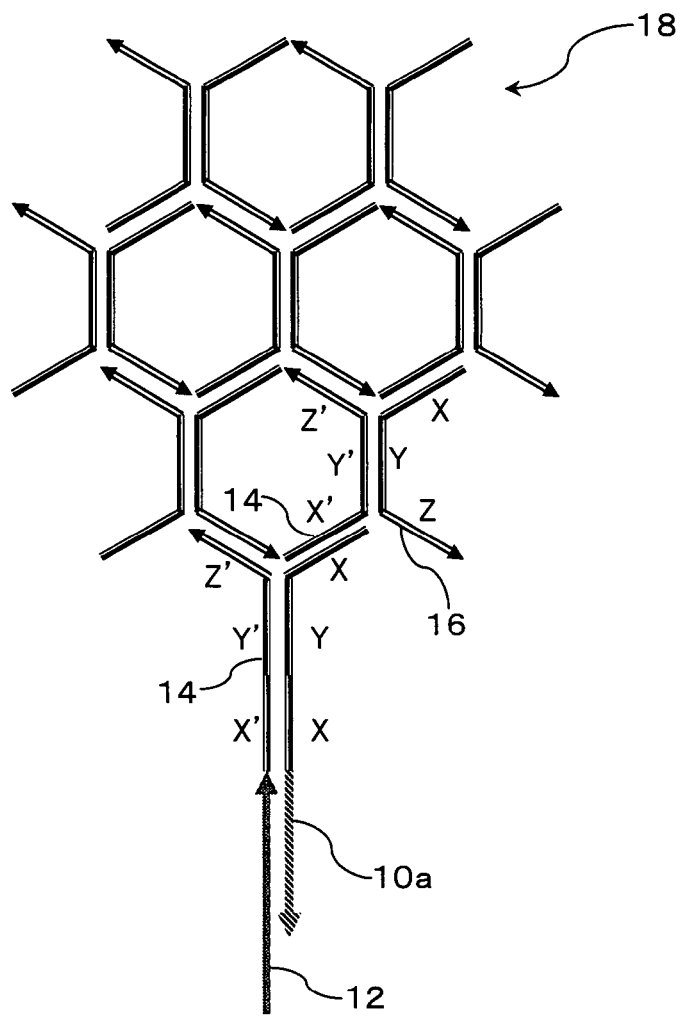
FIG. 3 is a schematic diagram illustrating an example of a method of forming a signal probe polymer by using the assist probe of FIG. 1.
Figure 4:
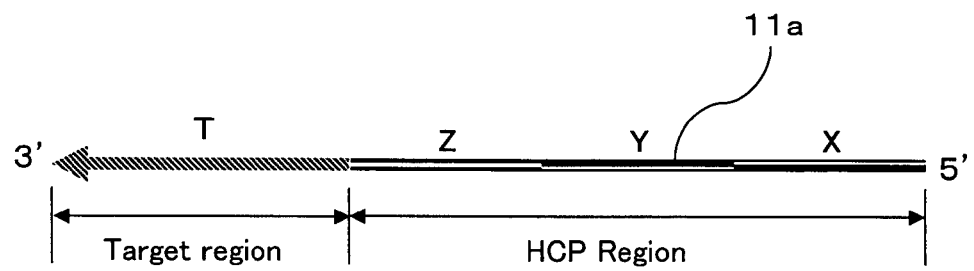
FIG. 4 is a schematic diagram illustrating an example of the assist probe.
Figure 5:
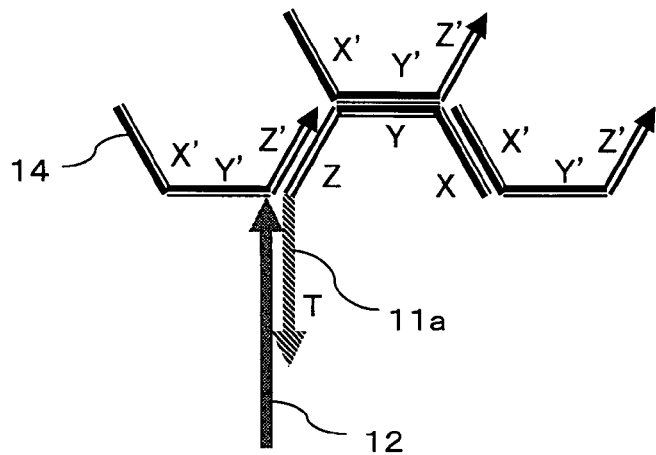
FIG. 5 is a schematic diagram illustrating a state where HCP-2 and a target gene bound to the assist probe of FIG. 4.
Figure 6:
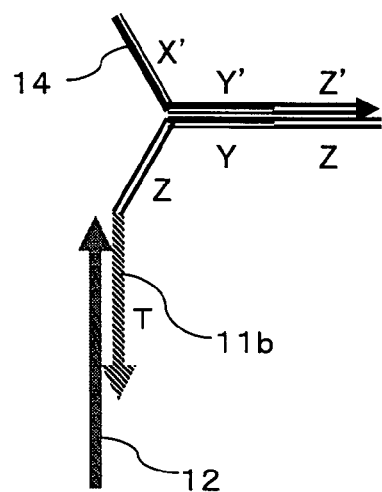
FIG. 6 is a schematic diagram illustrating another example of the assist probe.

FIG. 1 is a schematic diagram illustrating a first example of an assist probe of the present invention, and FIGS. 2 and 3 are schematic diagram illustrating examples of a method of forming a signal probe polymer using the assist probe of FIG. 1. FIG. 4 is a schematic diagram illustrating an example of a conventional assist probe, and FIG. 5 is a schematic diagram illustrating a state where a target gene and one of HCPs bind to the assist probe of FIG. 4. FIG. 6 is a schematic diagram illustrating another example of an assist probe.

The assist probe to be used in the PALSAR method includes one of HCPs (HCP-1) with no modification and a probe obtained by adding a sequence complementary to a target (target region) to one of HCPs (HCP-1) as shown in FIG. 4. The assist probe 11a of FIG. 4 has an HCP region including the same nucleic acid regions X, Y, and Z as in HCP-1 and a target region T complementary to a target gene, and as shown in FIG. 5, the HCP region binds to HCP-2s (symbol 14) at the respective regions. Note that, in the present invention, a region including a plurality of nucleic acid regions selected from the group consisting of the nucleic acid regions X, Y, and Z is referred to an HCP region.

An assist probe of the present invention is designed so as to bind to at least one HCP-2 at the two regions and to bind to another HCP-2 at the other regions.

FIG. 1 illustrates an example of an assist probe of the present invention. In FIG. 1, 10a illustrates a first example of an assist probe of the present invention, and the probe includes the target region T and HCP region including three regions, which is not XYZ but XYX from the 5' end (that is, 5'-XYX-T-3'). Therefore, when the HCP-2 (symbol 14) and assist probe 10a are allowed to react, as shown in FIG. 2, the assist probe binds to one HCP-2 at two sequential regions of the three regions and to another HCP-2 at the other region to form a polymer. Accordingly, as shown in FIG. 3, when plural pairs of HCPs (symbols 14 and 16), the assist probe 10a, and the target gene 12 are allowed to react, a signal probe polymer 18 including a complex of a polymer formed from a pair of HCPs, an assist probe and a target gene is formed.

However, as shown in FIG. 6, if an assist probe is designed so that the end on the HCP region side thereof corresponds to the end of HCP-2 in binding in the present invention, signals may decrease. Therefore, an assist probe should be designed so that the end on the HCP region side of the assist probe is different from the end of the HCP-2 in binding to the HCP-2. In FIG. 6, 11b is another example of an assist probe.

Figure 7:
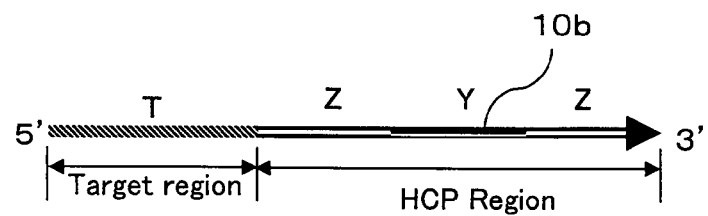
FIG. 7 is a schematic diagram illustrating a second example of the assist probe of the present invention.

FIG. 7 is a schematic diagram illustrating a second example of an assist probe of the present invention.

FIG. 1 illustrates an assist probe including a target region on the 3' side, but the positions of the target region and the HCP region are not particularly limited, and the present invention includes an assist probe including a target region on the 5' side. Examples of the assist probe including a target region on the 5' side include, as shown in FIG. 7, an assist probe 10b (5'-T-ZYZ-3') including a target region T on the 5' side and an HCP region that include three regions ZYZ on the 3' side.

Figure 8:
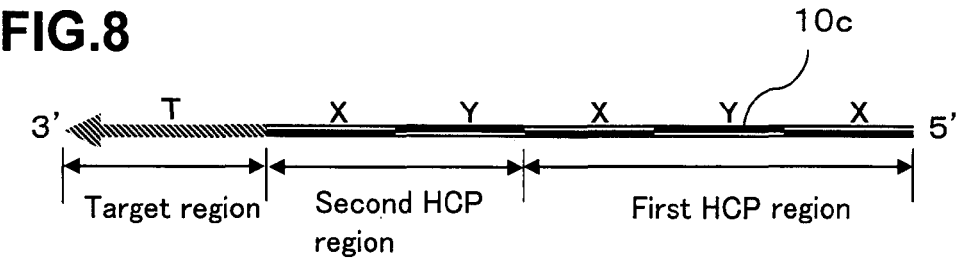
FIG. 8 is a schematic diagram illustrating a third example of the assist probe of the present invention.
Figure 9:
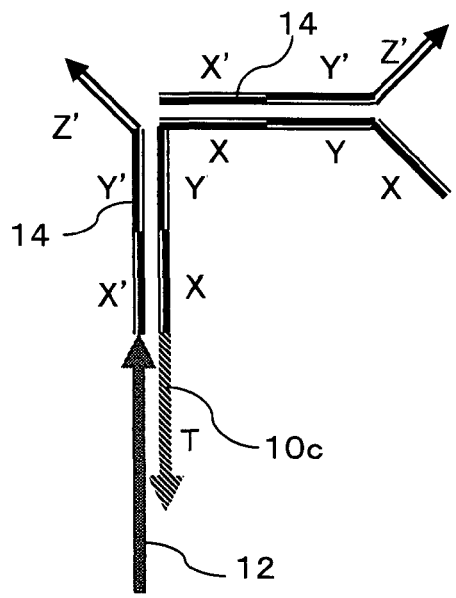
FIG. 9 is a schematic diagram illustrating a state where HCP-2 and a target gene bound to the assist probe of FIG. 8.
Figure 10:
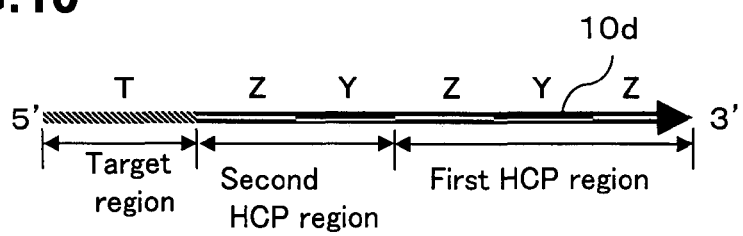
FIG. 10 is a schematic diagram illustrating a fourth example of the assist probe of the present invention.

FIG. 8 is a schematic view a third example of an assist probe of the present invention, and FIG. 9 is a schematic diagram illustrating a state where one of HCPs (HCP-2) and a target gene bind to the assist probe of FIG. 8. FIG. 10 is a schematic diagram illustrating a fourth example of an assist probe of the present invention.

As an assist probe of the present invention, there may be used a probe designed so that two or more of HCP-2s bind to one assist probe at sequential two regions.

Examples of the assist probe include, as shown in FIG. 8, an assist probe 10c (5'-XYX-YX-T-3') further including a second HCP region capable of binding to HCP-2 at sequential two regions and having two regions XY between the first HCP region (XYX) at the 5' end and the target region T at the 3' end. As shown in FIG. 9, when the assist probe 10c is allowed to react with HCP-2, one assist probe 10c binds to two HCP-2s at sequential two regions.

Meanwhile, as shown in FIG. 10, there may be used an assist probe 10d (5'-T-ZY-ZYZ-3') further including a second HCP region capable of binding to HCP-2 at sequential two regions and having two regions ZY between the target region T at the 5' end and the first HCP region (ZYZ) at the 3' end.

Note that FIGS. 8 and 10 show examples of assist probes further including a second HCP region, but an assist probe having a plurality of the second HCP regions may be used.

Figure 11:
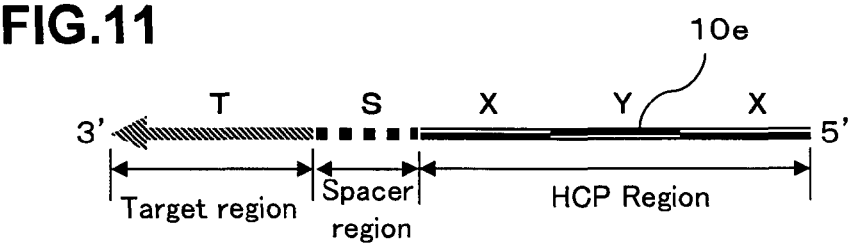
FIG. 11 is a schematic diagram illustrating a fifth example of the assist probe of the present invention.
Figure 12:
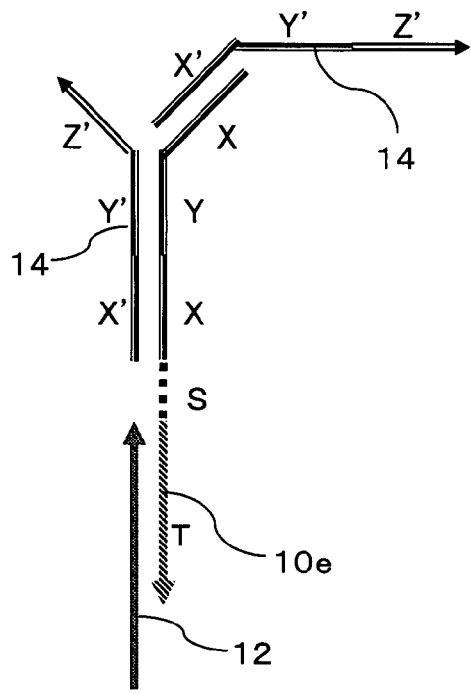
FIG. 12 is a schematic diagram illustrating a state where HCP-2 and a target gene bound to the assist probe of FIG. 11.

FIG. 11 is a schematic diagram illustrating a fifth example of an assist probe of the present invention, and FIG. 12 is a schematic diagram illustrating a state where one of HCPs (HCP-2) and a target gene bind to the assist probe of FIG. 11.

Figure 13:
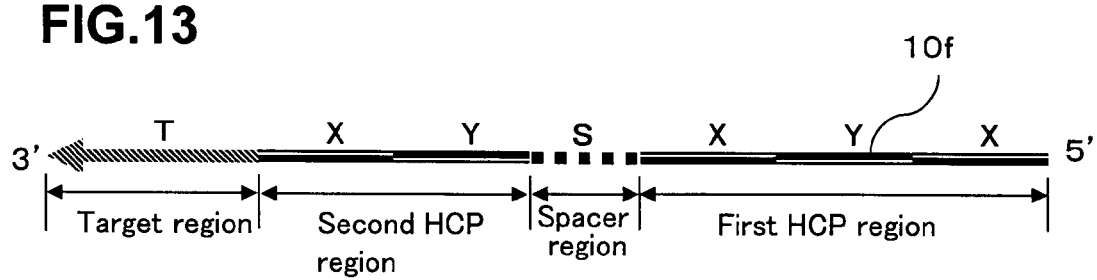
FIG. 13 is a schematic diagram illustrating a sixth example of the assist probe of the present invention.

FIG. 13 is a schematic diagram illustrating a sixth example of an assist probe of the present invention.

When an assist probe further including a spacer region S having a sequence (spacer sequence) unrelated to a target sequence or HCPs between a target region and an HCP region or between a first HCP region and a second HCP region is used as an assist probe of the present invention, sensitivity in signal detection may increase in some cases.

In an assist probe of the present invention, a number of bases in the spacer region is preferably 0 to 5 bases, but is not particularly limited thereto.

Examples of the assist probe having a spacer region include an assist probe further including a spacer region between the target region and the HCP region [5'-XYX-S-T-3' (see the assist probe 10e of FIG. 11) or 5'-T-S-ZYZ-3'], an assist probe further including a spacer region between the first HCP region and the second HCP region [5'-XYX-S-YX-T-3' (see the assist probe 10f of FIG. 13) or 5'-T-ZY-S-ZYZ-3'], an assist probe further including a spacer region between the target region and the second HCP region [5'-XYX-YX-S-T-3' or 5'-T-S-ZY-ZYZ-3'], and an assist probe further including spacer regions between the target region and the second HCP region and between the second HCP and the first HCP region [5'-XYX-S-YX-S-T-3' or 5'-T-S-ZY-S-ZYZ-3'].

Figure 14:
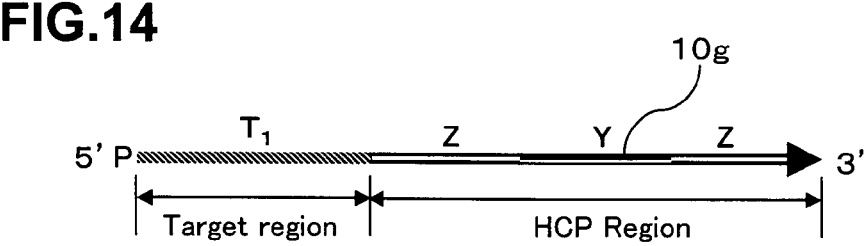
FIG. 14 is a schematic diagram illustrating a seventh example of the assist probe of the present invention.

FIG. 14 is a schematic diagram illustrating an example of an assist probe to be used in a method of detecting a target gene using a ligation reaction, and 10g represents a seventh example of an assist probe of the present invention. As shown in FIG. 14, an assist probe having phosphorylated 5' end at the target region is preferably used as an assist probe in a method of detecting a target gene using a ligation reaction (for example, see Patent Document 4, etc.).

One example of the method of detecting a target gene using a ligation reaction will be described below. FIGS. 15 to 18 are schematic diagram illustrating examples of the order of steps in a method of detecting a target gene using the assist probe of FIG. 14 and a ligation reaction.

Figure 15:
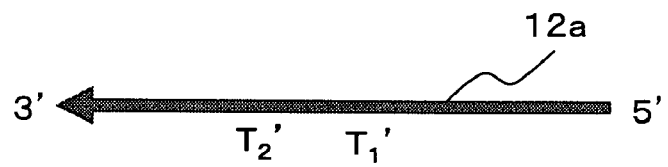
FIG. 15 is a schematic diagram illustrating an example of an order of steps in a method of detecting a target gene by using the assist probe of FIG. 14 and a ligation reaction, where (a) and (b) each represent a target gene and a capture probe bound to a support.
Figure 15:
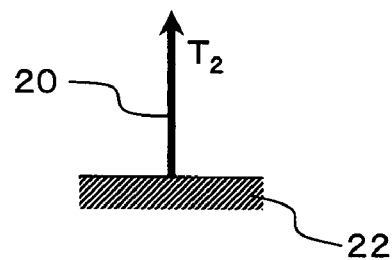
Figure 16:
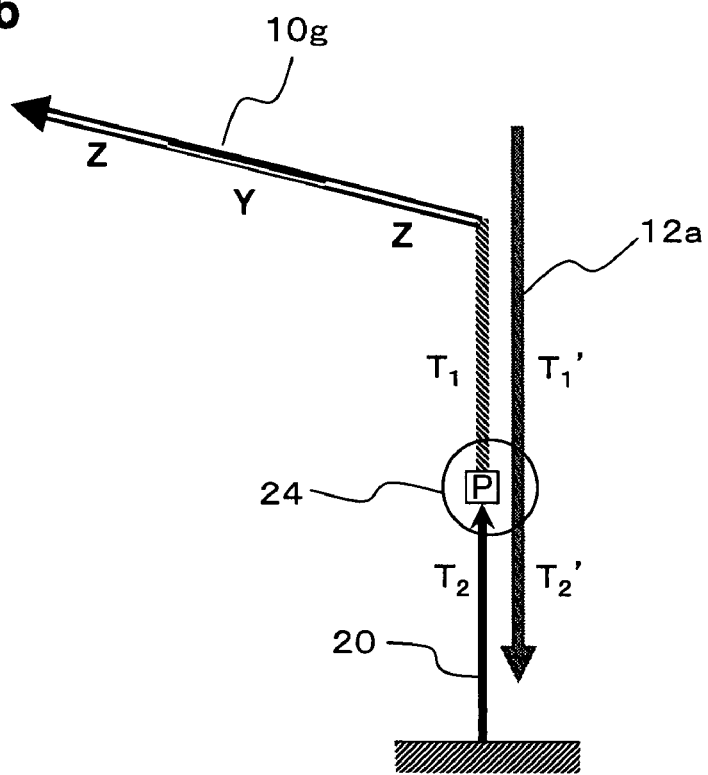
FIG. 16 is a schematic diagram illustrating a step 100 in an example of the order of steps in the method of detecting a target gene by using the assist probe of FIG. 14 and a ligation reaction.
Figure 17:
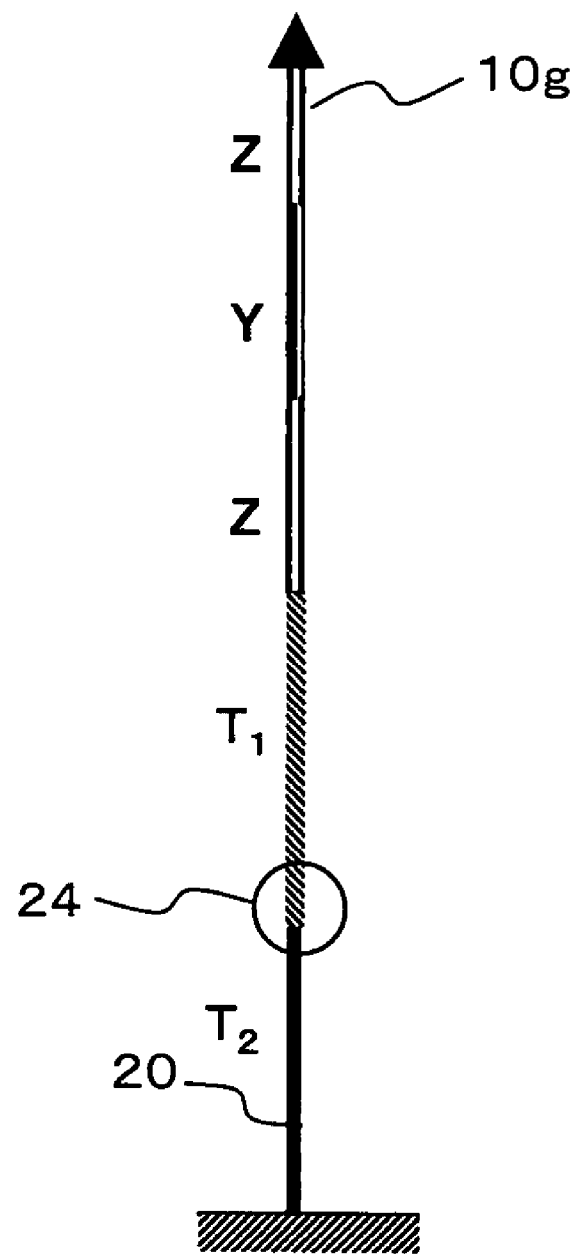
FIG. 17 is a schematic diagram illustrating a step 104 in an example of the order of steps in the method of detecting target a target gene by using the assist probe of FIG. 14 and the ligation reaction.

In FIG. 15, (a) represents a target gene (symbol 12a), and (b) represents a support 22 bound to a capture probe having a region $T_2$ complementary to the target gene on the 3' end side. FIG. 16 is a schematic diagram illustrating a state where an assist probe 10g, a capture probe 20, and a target gene 12a bind to each other. FIG. 17 illustrates a state where a capture probe 20 that is dissociated from the target gene 12a and is linked to an assist probe 10g binds to a support 24.

As shown in FIGS. 14 to 16, the assist probe 10g and capture probe 20 are designed so as to anneal to the target gene 12a in a state where the end of the capture probe 20 and the end of the assist probe 10g are adjacent to each other.

As shown in FIG. 16, the assist probe 10g and capture probe 20 are allowed to hybridize with the target gene 12a (step 100). Thereafter, a ligation reaction is carried out using a ligase (step 102). Only in the case where the sequence of the part 24 adjacent to the assist probe 10g and capture probe 20 is complementary to the sequence of the target gene 12a, the assist probe 10g and capture probe 20 are linked by a ligation reaction.

After the ligation reaction, the target gene 12a is removed (step 104). In the case where the sequence of the part 24 adjacent to the assist probe 10g and capture probe 20 is complementary to the sequence of the target gene 12a, as shown in FIG. 17, the capture probe 20 linked to the assist probe 10g binds to the support 24.

Figure 18:
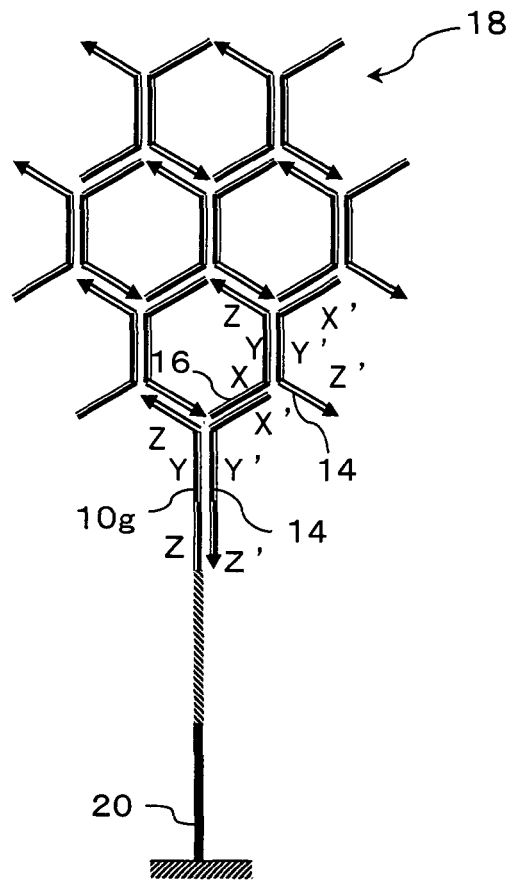
FIG. 18 is a schematic diagram illustrating a step 106 in an example of the order of steps in the method of detecting a target gene by using the assist probe of FIG. 14 and the ligation reaction.

Thereafter, when plural pairs of HCPs (14 and 16) are added to carry out a hybridization reaction (step 106), as shown in FIG. 18, a signal probe polymer 18 including a complex of a polymer formed from a pair of HCPs, an assist probe and a target gene is formed on the support.

On the other hand, in the case where the sequence of the part 24 adjacent to the assist probe 10g and capture probe 20 is not complementary to the sequence of a target gene, the assist probe 10g and capture probe 20 are not linked after the step 102. When the target gene is removed, only the capture probe 20 binds to the support 24. Therefore, after the step, polymers formed by adding plural pairs of HCPs are not captured on the support and removed by washing or the like.

Accordingly, detection of a signal probe polymer captured on a support can detect a target gene. In particular, an assist probe designed so that the part 24 adjacent to the assist probe 10g and capture probe 20 will be positioned on a mutation site of the target gene can detect a mutant gene.

Figure 19:
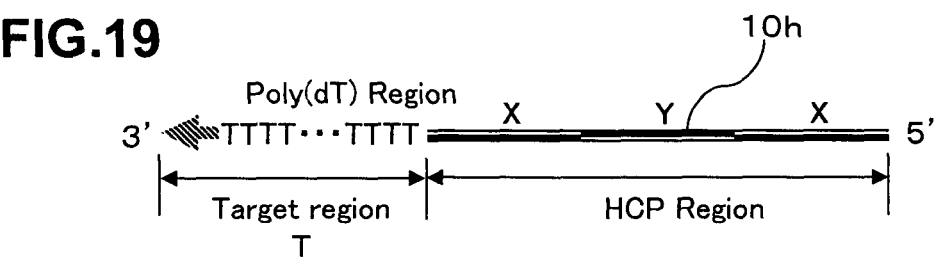
FIG. 19 is a schematic diagram illustrating an eighth example of the assist probe of the present invention.
Figure 20:
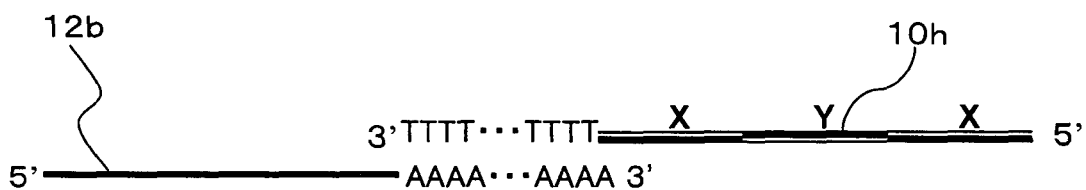
FIG. 20 is a schematic diagram illustrating a step 200 in an example of the order of steps in the method of detecting a target gene by using the assist probe of FIG. 19 and the reverse transcription reaction.

FIG. 19 is a schematic diagram illustrating an example of an assist probe to be used in a method of detecting a target gene using a reverse transcription reaction, and 10h represents an eighth example of an assist probe of the present invention. As shown in FIG. 15, an assist probe having a sequence that may be used as a primer for a reverse transcription reaction such as poly(dT) sequence at the target region on the 3' end side is preferably used as an assist probe in a method of detecting a target gene using a reverse transcription reaction (for example, see Patent Document 5, etc.).

One example of the method of detecting a target gene using a reverse transcription reaction will be described below. FIGS. 20 to 23 are schematic diagrams illustrating examples of the orders of steps in a method of detecting a target gene using an assist probe and a reverse transcription reaction. FIGS. 20 to 23 show examples of the case where the target gene is mRNA, and an assist probe 10h having poly(dT) on a target region at the 3' end and including HCP region having three regions XYX on the 5' side is used as an assist probe.

Figure 21:
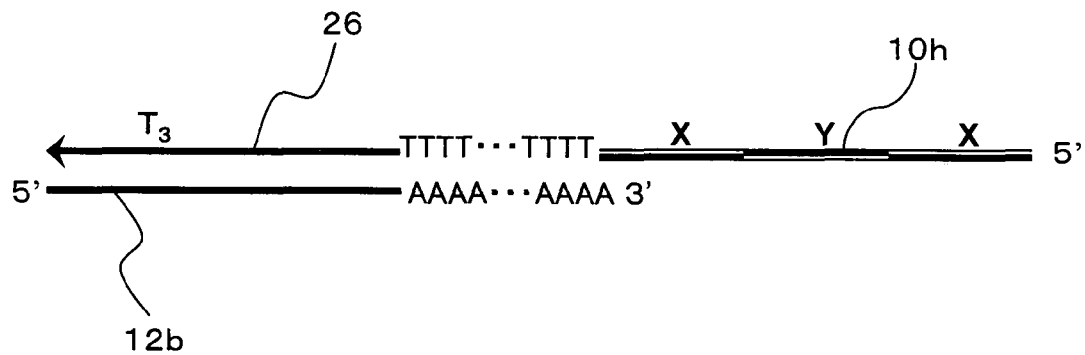
FIG. 21 is a schematic diagram illustrating a step 202 in an example of the order of steps in the method of detecting a target gene by using the assist probe of FIG. 19 and a reverse transcription reaction.

The assist probe 10h including poly(dT) at the 3' end is allowed to bind to the polyA tail part of a target gene, i.e., mRNA (symbol 12b) (step 200, FIG. 20), and the assist probe 10h is used as a primer to carry out a reverse transcription reaction for the mRNA, to thereby form a probe 26 including the assist probe and the cDNA region of the mRNA (step 202, FIG. 21).

Figure 22:
FIG. 22 is a schematic diagram illustrating a step 204 in an example of the order of steps in the method of detecting a target gene by using the assist probe of FIG. 19 and the reverse transcription reaction.

Next, as shown in FIG. 22, the mRNA is dissociated from the probe 26, to thereby yield a single-stranded oligonucleotide having the cDNA region and HCP region XYX (step 204).

Figure 23:
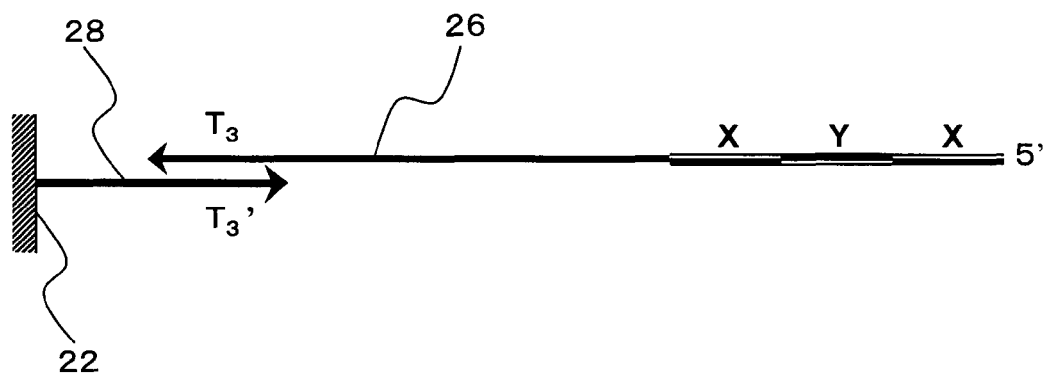
FIG. 23 is a schematic diagram illustrating a step 206 in an example of the order of steps in the method of detecting a target gene by using the assist probe of FIG. 19 and the reverse transcription reaction.

After the dissociation, the probe 26 is allowed to hybridize with a capture probe 28 having a region complementary to the cDNA region of the mRNA to capture the probe 26 (step 206, FIG. 23). Note that the capture probe is preferably allowed to bind to the support 22 in advance.

Thereafter, a hybridization reaction is carried out by adding plural pairs of HCPs (step 208), to thereby form a signal probe polymer captured by the capture probe 28. If the signal probe polymer is detected, a target gene can be detected.

EXAMPLES

Hereinafter, the present invention will be described more specifically by way of Examples, but it will be appreciated that these Examples are for illustrative purposes only and should not be construed as limiting the scope of the invention.

Example 1

1. Materials

Oligonucleotide probes having the following base sequences with the 5' ends labeled with Cy3 (HCP-1A and HCP-2A) were used as a pair of HCPs to be used in the PALSAR method.

```
Base sequence of HCP-1A (SEQ ID NO: 1)
 5'-Cy3-X region    (CGTATCAATGATAGCCGATC)

Y region           (CGCCTAAGTTCGATATAGTC)

Z region           (CGCGTATACTAAGCGTAATG)-3'

Base sequence of HCP-2A (SEQ ID NO: 2)
 5'-Cy3-X' region   (GATCGGCTATCATTGATACG)

Y' region          (GACTATATCGAACTTAGGCG)

Z' region          (CATTACGCTTAGTATACGCG)-3'
```

A synthetic DNA having a base sequence derived from Apolipoprotein E (ApoE) (target DNA-1) was used as a target DNA.

```
Base sequence of target DNA-1 (SEQ ID NO: 3)
5'-GGCGGAGGAGACGCGGGCACGGCTGTCCAAGGAGCTGCAGGCGGCGC

AGGCCCGGCTGGGCGCGGACATGGAGGACGTGTGCGGCCGCCTGGTGCAG

TACCGCGGCGAGGTGCAGGCCAT-3'
```

The following assist probe-1 was used as an assist probe, which includes two of three regions of the HCP-1A in XYX order and has a region of a sequence complementary to that of the target DNA-1 at the 3' end (T region).

```
Base sequence of assist probe-1 (SEQ ID NO: 4)
 5'-X region        (CGTATCAATGATAGCCGATC)

Y region           (CGCCTAAGTTCGATATAGTC)

X region           (CGTATCAATGATAGCCGATC)

T region           (GTACTGCACCAGGCGGCCGC)-3'
```

The following capture probe-1 was used as a capture probe, which has a base sequence complementary to that of the target DNA-1.

```
Base sequence of capture probe-1 (SEQ ID NO: 5)
5'-ACACGTCCTCCATGTCCGCGCCCAGCCGGGCCTGCGCCGCCTGCAGC

TCCTTGGACAGCCG-NH₂-3'
```

2. Methods (2-1) First Hybridization

A first hybridization solution having the following composition (total volume: 50 μL) was prepared and allowed to react at 95° C. for two minutes and then at 68° C. for 120 minutes, followed by incubation at 15° C.

<Composition of First Hybridization Solution>
Fine particles (polystyrene particles with the surfaces immobilized with the capture probe-1): 500 particles
assist probe-1: 1 pmol
target DNA-1: 0, 100, or 500 amol
3M TMAC
0.1% N-Lauroylsarcosine
50 mM Tris-HCl (pH 8.0)
4 mM EDTA (pH 8.0)

(2-2) Second Hybridization (PALSAR Method)

After the first hybridization, 50 µL of an HCP solution was added to the resultant solution to achieve the following composition (final volume: 100 µL), and the mixture was allowed to react at 68° C. for 60 minutes, followed by incubation at 15° C. Note that the HCP solution was subjected to a thermal treatment at 95° C. for two minutes before addition.

(Composition of Second Hybridization Solution)
HCP-1A: 50 pmol
HCP-2A: 50 pmol
3M TMAC
0.1% N-Lauroylsarcosine
50 mM Tris-HCl (pH 8.0)
4 mM EDTA (pH 8.0)

(2-3) Measurement

After the second hybridization, measurement was carried out using a flow cytometer. Fluorescence intensities of about 100 fine particles were measured for each item using Luminex 100 (manufactured by Luminex Corporation) as a flow cytometer, followed by calculation of medians. The results are shown in Table 1. Note that the numerical values were calculated by subtracting blank values from actual measured values.

TABLE 1

| Concentration of target DNA (amol) | Example 1 | Example 2 | Comparative Example 1 |
|---|---|---|---|
| 0 | 0 | 0 | 0 |
| 100 | 1268 | 4301 | 273 |
| 500 | 19099 | 20112 | 15988 |

Example 2

The experiment of Example 1 was repeated except that the following assist probe-2, which was obtained by inserting a spacer region S including five poly(dT)s and a YX region between the XYX region and the T region of the assist probe-1, was used as an assist probe. The results are shown in Table 1.

```
Base sequence of assist probe-2 (SEQ ID NO: 6)
5'-X region      (CGTATCAATGATAGCCGATC)

Y region         (CGCCTAAGTTCGATATAGTC)

X region         (CGTATCAATGATAGCCGATC)

S region         (TTTTT)

Y region         (CGCCTAAGTTCGATATAGTC)

X region         (CGTATCAATGATAGCCGATC)

T region         (GTACTGCACCAGGCGGCCGC)-3'
```

Comparative Example 1

The experiment of Example 1 was repeated except that the following assist probe-3 (a conventional assist probe) was used as an assist probe.

The results are shown in Table 1.

```
Base sequence of assist probe-3 (SEQ ID NO: 7)
5'-X region      (CGTATCAATGATAGCCGATC)

Y region         (CGCCTAAGTTCGATATAGTC)

Z region         (CGCGTATACTAAGCGTAATG)

T region         (GTACTGCACCAGGCGGCCGC)-3'
```

As shown in Table 1, in the cases of Examples 1 and 2 where the assist probes of the present invention were used, the signals were found to be significantly larger than those in the case of Comparative Example 1 where the conventional assist probe was used.

The invention claimed is:

1. A method of detecting a target gene, comprising forming a signal probe polymer by contacting:
 - a pair of first and second probes:
   - the first probe having three nucleic acid regions, which includes a nucleic acid region X, a nucleic acid region Y, and a nucleic acid region Z in the stated order from the 5' end;
   - the second probe having three nucleic acid regions, which includes a nucleic acid region X', a nucleic acid region Y', and a nucleic acid region Z' in the stated order from the 5' end;
 - wherein the nucleic acid regions X and X', the nucleic acid regions Y and Y', and the nucleic acid regions Z and Z' are complementary regions capable of hybridizing with each other, respectively;
 - an assist probe having a plurality of the same nucleic acid regions as in the first probe and a target region capable of hybridizing with a target gene;
 - wherein the assist probe comprises the nucleic acid regions X, Y, and X, and the target region in the stated order from the 5' end, or comprises the target region, and the nucleic acid regions Z, Y, and Z in the stated order from the 5' end; and
 - the target gene;
 - wherein the nucleic acid regions X and X', the nucleic acid regions Y and Y', and the nucleic acid regions Z and Z' of the pair of first and second probes and the assist probe hybridize to each other and wherein the target gene is detected.

2. The method of detecting a target gene according to claim 1, wherein the assist probe further comprises a spacer region incapable of hybridizing with the target gene and the first and second probes between the target region and the nucleic acid region X or Z.

3. The method of detecting a target gene according to claim 1, wherein the assist probe comprises an XYX region having the nucleic acid regions X, Y, and X, a YX region having the nucleic acid regions Y and X, and the target region in the stated order from the 5' end, or comprises the target region, a ZY region having the nucleic acid regions Z and Y, and a ZYZ region having the nucleic acid regions Z, Y, and Z in the stated order from the 5' end.

4. The method of detecting a target gene according to claim 3, wherein the assist probe further comprises a spacer region incapable of hybridizing with the target gene and the first and second probes between the XYX region and the YX region or between the ZY region and the ZYZ region.

5. The method of detecting a target gene according to claim 1, further comprising a reaction step of ligating the assist probe by using the target gene as a template.

6. The method of detecting a target gene according to claim 1, further comprising a reaction step of performing reverse transcription by using an assist probe having poly(dT) or a primer sequence on the target region of the 3' end as a primer and by using a target RNA as a template.

7. The method of detecting a target gene according to claim 1, wherein a plurality of target genes are simultaneously detected by using a plurality of assist probes, which are different from each other only in the target regions.

8. A method of forming a signal probe polymer, comprising:
 - providing a pair of first and second probes including:
   - the first probe having three nucleic acid regions, includes a nucleic acid region X, a nucleic acid region Y, and a nucleic acid region Z in the stated order from the 5' end;
   - the second probe having three nucleic acid regions, which includes a nucleic acid region X', a nucleic acid region Y', and a nucleic acid region Z' in the stated order from the 5' end;
 - wherein the nucleic acid regions X and X', the nucleic acid regions Y and Y', and the nucleic acid regions Z and Z' are complementary regions capable of hybridizing with each other, respectively; and
 - an assist probe having a plurality of the same nucleic acid regions as in the first probe and a target region capable of hybridizing with a target gene; and
 - wherein the nucleic acid regions X and X', the nucleic acid regions Y and Y', and the nucleic acid regions Z and Z' of the plural pairs of the first and second probes, the assist probe, and the target gene hybridize with each other, and
 - wherein the assist probe comprises the nucleic acid regions X, Y, and X, and the target region in the stated order from the 5' end, or comprises the target region, and the nucleic acid regions Z, Y, and Z in the stated order from the 5' end.

* * * * *

SEQUENCE LISTING

```
<160> NUMBER OF SEQ ID NOS: 7

<210> SEQ ID NO 1
<211> LENGTH: 60
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: Cy3 attached at the 5' end

<400> SEQUENCE: 1
cgtatcaatg atagccgatc cgcctaagtt cgatatagtc cgcgtatact aagcgtaatg    60

<210> SEQ ID NO 2
<211> LENGTH: 60
<212> TYPE: DNA
```

-continued

<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: Cy3 attached at the 5' end

<400> SEQUENCE: 2
gatcggctat cattgatacg gactatatcg aacttaggcg cattacgctt agtatacgcg      60

<210> SEQ ID NO 3
<211> LENGTH: 120
<212> TYPE: DNA
<213> ORGANISM: Artificial
<220> FEATURE:
<223> OTHER INFORMATION: Description of Artificial Sequence; Synthetic

<400> SEQUENCE: 3
ggcggaggag acgcgggcac ggctgtccaa ggagctgcag gcggcgcagg cccggctggg      60
cgcggacatg gaggacgtgt gcggccgcct ggtgcagtac cgcggcgagg tgcaggccat     120

<210> SEQ ID NO 4
<211> LENGTH: 80
<212> TYPE: DNA
<213> ORGANISM: Artificial
<220> FEATURE:
<223> OTHER INFORMATION: Description of Artificial Sequence; Synthetic

<400> SEQUENCE: 4
cgtatcaatg atagccgatc cgcctaagtt cgatatagtc cgtatcaatg atagccgatc      60
gtactgcacc aggcggccgc                                                 80

<210> SEQ ID NO 5
<211> LENGTH: 61
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (61)..(61)
<223> OTHER INFORMATION: amino group attached at the 3' end

<400> SEQUENCE: 5
acacgtcctc catgtccgcg cccagccggg cctgcgccgc ctgcagctcc ttggacagcc      60
g                                                                     61

<210> SEQ ID NO 6
<211> LENGTH: 125
<212> TYPE: DNA
<213> ORGANISM: Artificial
<220> FEATURE:
<223> OTHER INFORMATION: Description of Artificial Sequence; Synthetic

<400> SEQUENCE: 6
cgtatcaatg atagccgatc cgcctaagtt cgatatagtc cgtatcaatg atagccgatc      60
tttttcgcct aagttcgata tagtccgtat caatgatagc cgatcgtact gcaccaggcg     120
gccgc                                                                125

<210> SEQ ID NO 7
<211> LENGTH: 80
<212> TYPE: DNA
<213> ORGANISM: Artificial

-continued

```
<220> FEATURE:
<223> OTHER INFORMATION: Description of Artificial Sequence; Synthetic

<400> SEQUENCE: 7
cgtatcaatg atagccgatc cgcctaagtt cgatatagtc cgcgtatact aagcgtaatg      60
gtactgcacc aggcggccgc                                                  80
```